US010507118B2

(12) United States Patent
Afzal

(10) Patent No.: US 10,507,118 B2
(45) Date of Patent: Dec. 17, 2019

(54) 3D PRINTED OSTEOGENESIS SCAFFOLD

(71) Applicant: Thomas Afzal, Menlo Park, CA (US)

(72) Inventor: Thomas Afzal, Menlo Park, CA (US)

(73) Assignee: MCA Group, LLC, Menlo Park, CA (US)

( * ) Notice: Subject to any disclaimer, the term of this patent is extended or adjusted under 35 U.S.C. 154(b) by 0 days.

(21) Appl. No.: 15/947,620

(22) Filed: Apr. 6, 2018

(65) Prior Publication Data

US 2019/0076268 A1   Mar. 14, 2019

Related U.S. Application Data

(63) Continuation of application No. 15/299,347, filed on Oct. 20, 2016, now abandoned.

(60) Provisional application No. 62/244,374, filed on Oct. 21, 2015.

(51) Int. Cl.
| | | |
|---|---|---|
| *A61F 2/44* | (2006.01) |
| *A61B 17/72* | (2006.01) |
| *A61F 2/30* | (2006.01) |
| *A61B 17/00* | (2006.01) |

(52) U.S. Cl.
CPC ............ *A61F 2/4465* (2013.01); *A61B 17/72* (2013.01); *A61F 2/4455* (2013.01); *A61B 2017/00862* (2013.01); *A61F 2002/3008* (2013.01); *A61F 2002/30062* (2013.01); *A61F 2002/30069* (2013.01); *A61F 2002/30187* (2013.01); *A61F 2002/30571* (2013.01); *A61F 2002/30593* (2013.01); *A61F 2002/30985* (2013.01); *A61F 2002/4475* (2013.01); *A61F 2002/4495* (2013.01)

(58) Field of Classification Search
CPC .................. A61F 2/4465; A61F 2/4455; A61F 2002/30062; A61F 2002/30069; A61F 2002/3008; A61F 2002/30187; A61F 2002/30571; A61F 2002/30593; A61F 2002/30985; A61F 2002/4475; A61F 2002/4495; A61B 17/72; A61B 2017/00862
USPC ....................................................... 623/17.16
See application file for complete search history.

(56) References Cited

U.S. PATENT DOCUMENTS

| | | | |
|---|---|---|---|
| 9,549,823 B2 | 1/2017 | Hunt et al. |
| 9,636,226 B2 | 5/2017 | Hunt |
| 9,918,849 B2 | 3/2018 | Morris et al. |
| 9,987,137 B2 | 6/2018 | Hunt et al. |
| 9,999,516 B2 | 6/2018 | Hunt |
| 10,213,317 B2 | 2/2019 | Bishop et al. |
| 10,357,377 B2 | 7/2019 | Nyahay et al. |
| 2003/0078667 A1 | 4/2003 | Manasas et al. |
| 2005/0015154 A1 | 1/2005 | Lindsey et al. |

(Continued)

*Primary Examiner* — Pedro Philogene
*Assistant Examiner* — David C Comstock
(74) *Attorney, Agent, or Firm* — Knobbe, Martens, Olson & Bear, LLP

(57) ABSTRACT

Osteogenesis scaffold such as for spinal fusion or an intermedullary nail includes a number of arcuate struts. The scaffold may have a functional modulus of elasticity that is a result of the modulus of the material of the struts together with the architecture of the struts, and may be within the range of 5 GPa and 75 GPa. An anisotropy of a physical property such as stiffness, compressive strength or elastic modulus corresponds to the same physical property of native bone in the vicinity of the intended implantation site.

18 Claims, 5 Drawing Sheets

(56) References Cited

U.S. PATENT DOCUMENTS

| | | |
|---|---|---|
| 2010/0137990 A1 | 6/2010 | Apatsidis et al. |
| 2014/0107785 A1 | 4/2014 | Geisler et al. |
| 2014/0107786 A1* | 4/2014 | Geisler ............... A61F 2/30965 623/17.16 |
| 2016/0081809 A1 | 3/2016 | Schneider et al. |
| 2016/0324656 A1* | 11/2016 | Morris ................ A61F 2/30744 |
| 2017/0042697 A1* | 2/2017 | Mcshane, III ...... A61F 2/30744 |
| 2018/0110626 A1 | 4/2018 | McShane, III et al. |
| 2018/0256353 A1 | 9/2018 | Nyahay et al. |

* cited by examiner

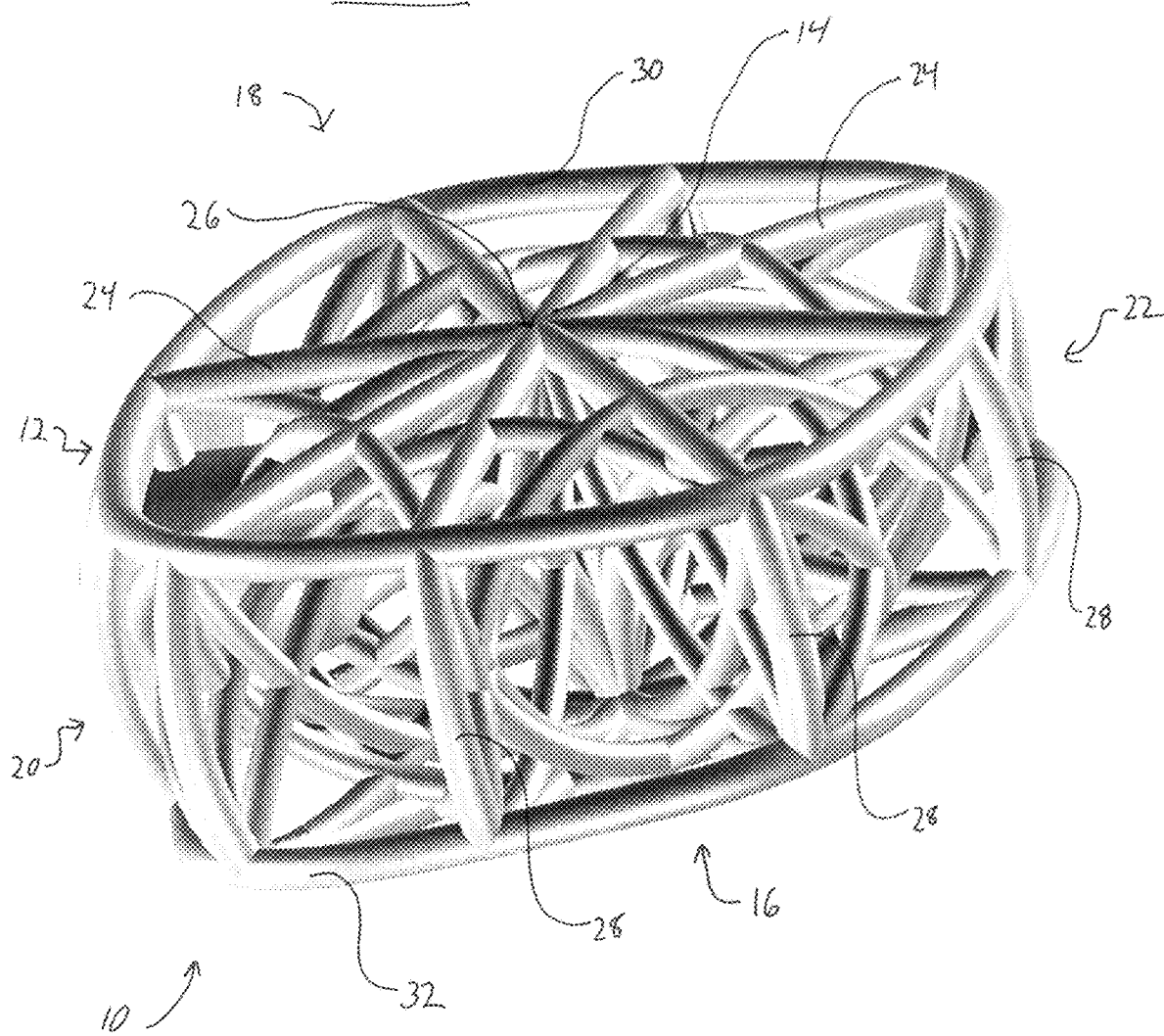

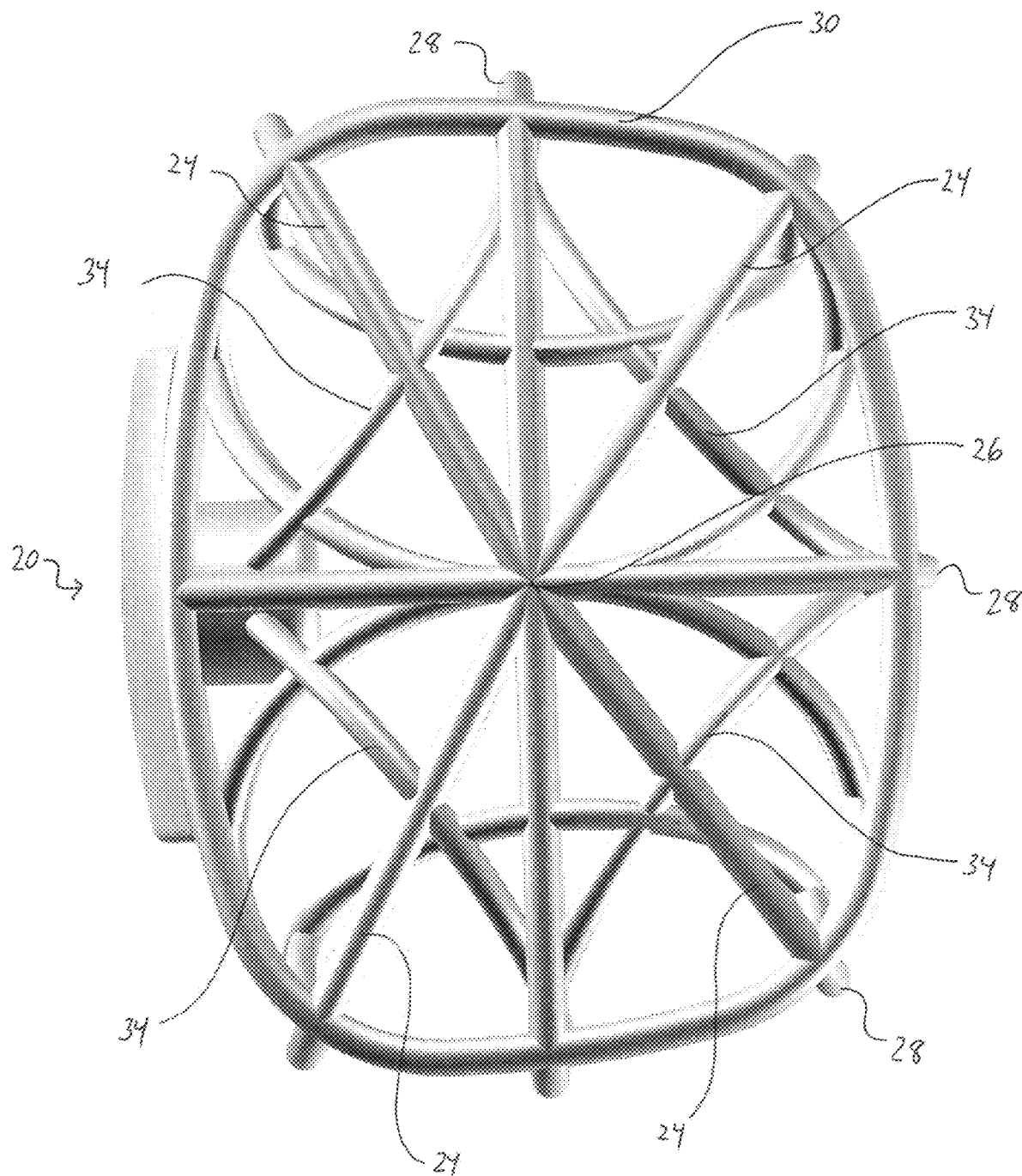

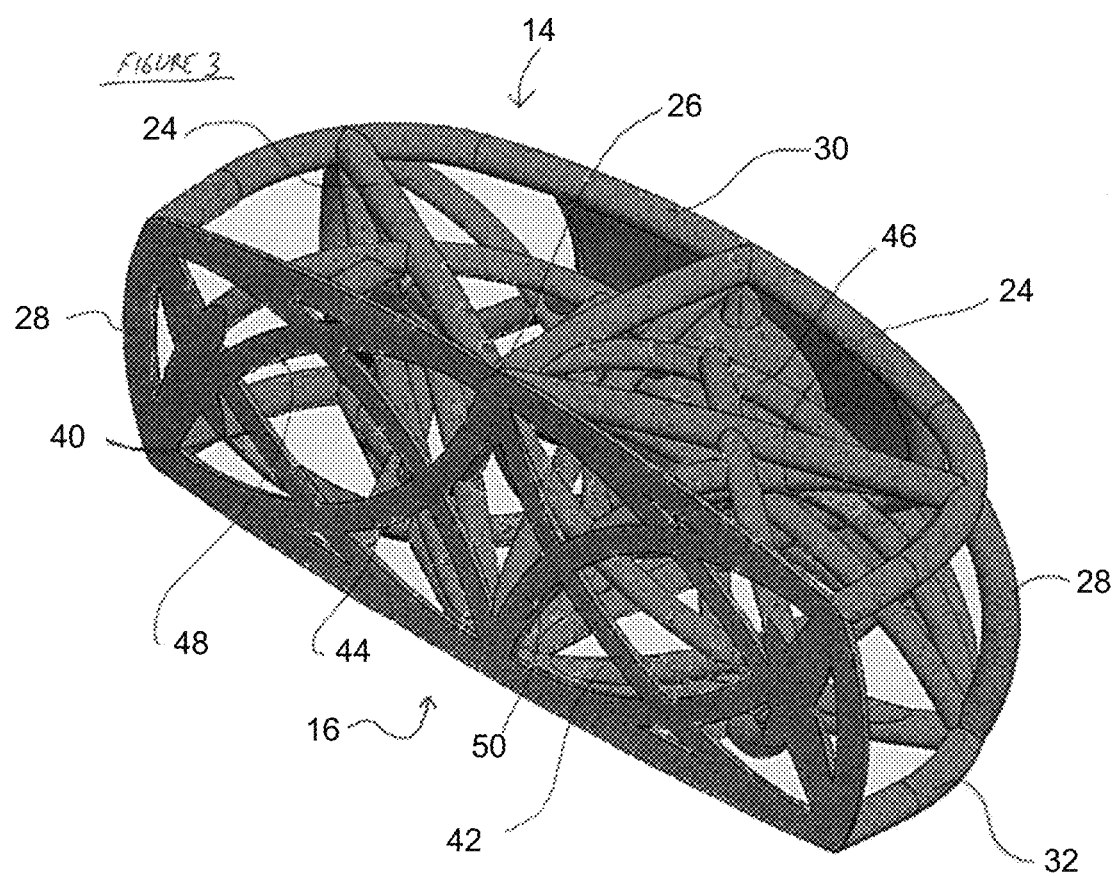

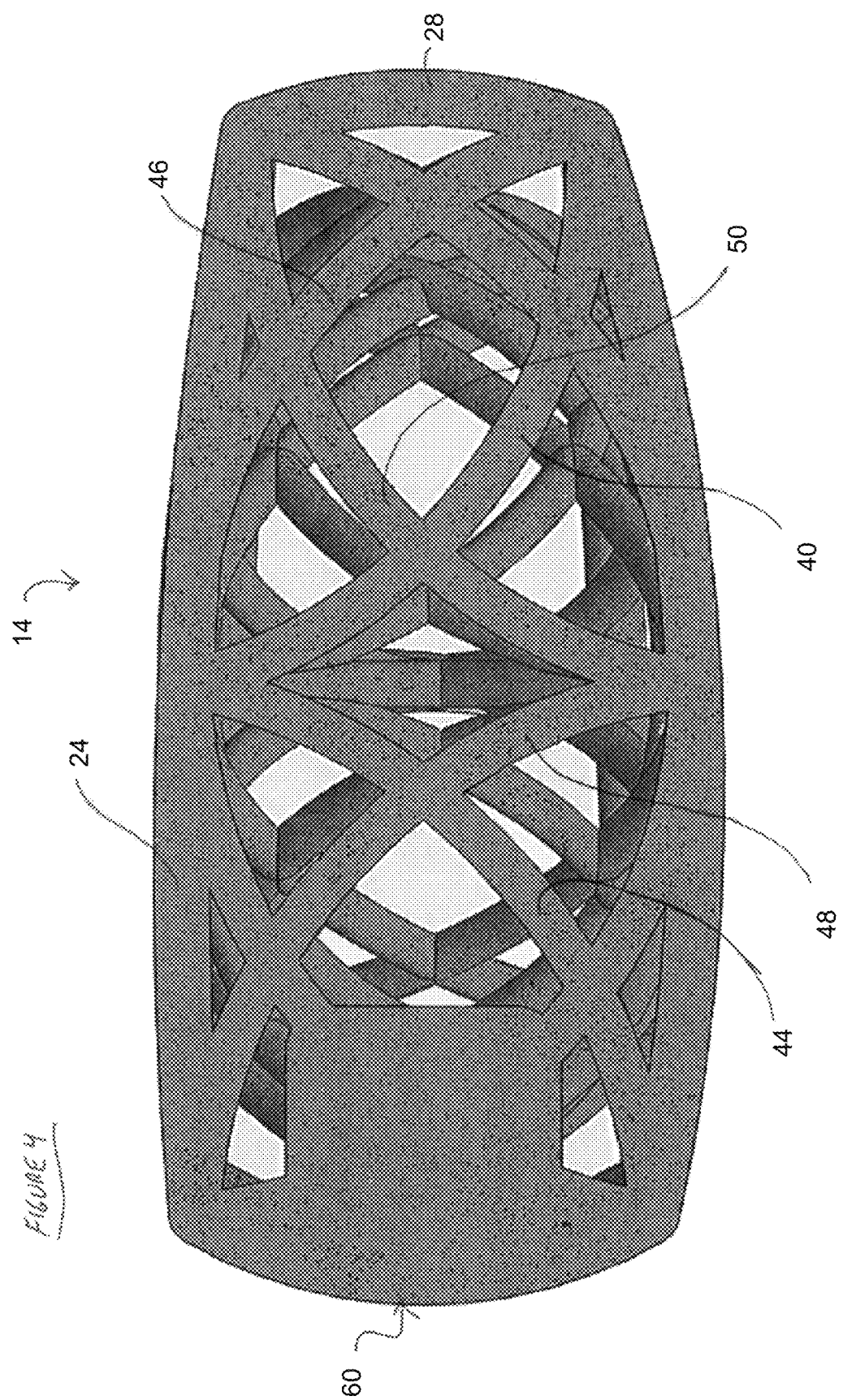

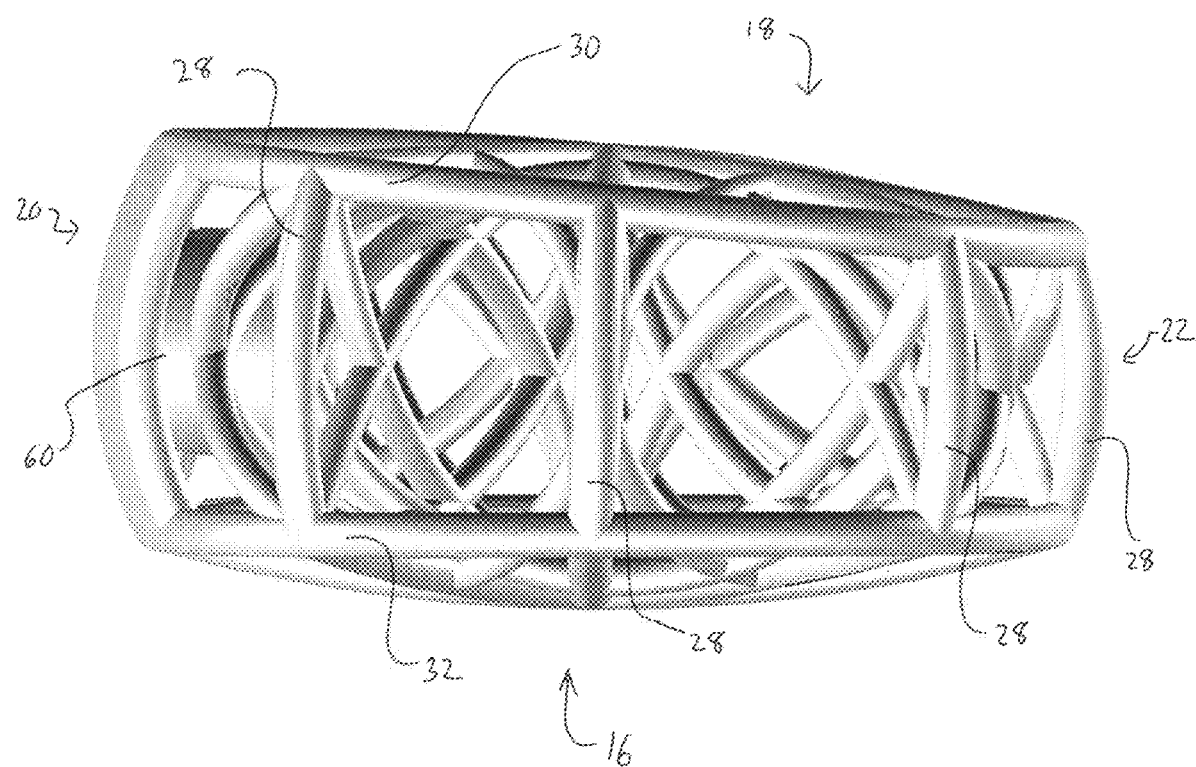

3D PRINTED OSTEOGENESIS SCAFFOLD

CROSS-REFERENCE TO RELATED APPLICATIONS

This application is a continuation application of U.S. application Ser. No. 15/299,347, filed Oct. 20, 2016, which claims the priority benefit under 35 U.S.C. § 119(e) of U.S. Provisional Application No. 62/244,374, filed Oct. 21, 2015, the entirety of which is hereby incorporated by reference herein.

BACKGROUND OF THE INVENTION

Spondylosyndesis, or spinal fusion, is a surgical technique used to combine two or more vertebrae into a single, rigid working unit. This is typically achieved by introducing a supplementary bone tissue, such as an autograft or allograft, into the intervertebral space between two target vertebrae, at the location that is typically occupied by an intervertebral disc. The supplementary bone tissue is then used in conjunction with the patient's natural osteoblastic processes in order to grow bone or osseous tissue between the two or more target vertebrae, which acts to fuse them together into the desired rigid unit. This procedure is used primarily to eliminate pain that is caused by abnormal motion of one or both of the target vertebrae; pain relief occurs by immobilizing the vertebrae themselves and preventing the abnormal motion. Alternatively, surgically implantable synthetic intervertebral fusion cages or devices may be used to perform spinal fusion procedures.

Surgically implantable intervertebral fusion cages are well known in the art and have been actively used to perform spinal fusion procedures for many years. Their use became popularized during the mid 1990's with the introduction of the BAK Device from the Zimmer Inc. The BAK system is a fenestrated, threaded, cylindrical, titanium alloy device that is capable of being implanted into a patient as described above through an anterior or posterior approach, and is indicated for cervical and lumbar spinal surgery. Most common spinal fusion systems today are made from metals, such as titanium or cobalt chrome alloys, or from a polymer such as polyetheretherketone (PEEK) which is commonly used in biomedical implants. Unfortunately, these implant materials have a modulus which is much higher than that of bone and there is clinical evidence of implant subsidence and movement which is believed to be attributable to mechanical incompatibility between natural bone and the implant material. Also bone pressure necrosis does occur as a result of the presence of these metal implants.

Implants based on bone material from a donor (allograft) or from the patient itself (autograft) do have an inconsistent mechanical strength and show subsidence over time. The inconsistent properties of these implants make them generally unpredictable, challenging to reliably machine and especially prone to migration and expulsion due to the difficulty of consistently machining teeth into the upper and lower implant contact surfaces.

Although titanium alloy cages give good fusion rates, their modulus is significantly dissimilar to human bone. The stress transfer between an implant device and a bone is not homogeneous when Young's moduli of the implant device and the bone are different. This results in stress shielding. In such conditions, bone atrophy occurs and leads to the loosening of at the implant bone interface and eventually lead to failure. Therefore, the stiffness (Young's modulus) of the implant is preferably not too high compared to that of bone. Implant devices made from metallic biomaterials such as stainless steels, Co—Cr alloys, and titanium (Ti) and its alloys have a Young's modus generally much greater than that of the bone. Young's moduli of the most widely used stainless steel for implant devices, SUS316L stainless steel and Co—Cr alloys, are around 180 GPa and 210 GPa, respectively. Young's moduli of Ti (pure titanium) and its alloys are generally smaller than those of stainless steels and Co—Cr alloys. For example, Ti and its alloy, Ti-6Al-4V ELI, which are widely used for constructing implant devices, have a Young's modulus of around 110 GPa. However, this value is still higher than that of the bone, which is on the order of 10-30 GPa.

The foregoing shortcomings in the spinal fusion cage arts apply to other orthopedic implants as well, such as intermedullary nails for long bones such as the femur.

Therefore, there remains a need for a biostable implant such as for use as an orthopedic implant or plate which has a tensile modulus comparable to that of bone, which does not subside and provides a good stability.

BRIEF DESCRIPTION OF THE DRAWINGS

FIG. 1 is a side elevational perspective view of an implant in accordance with the present invention, in the form of a spinal fusion cage.

FIG. 2 is a top plan view of the spinal fusion cage shown in FIG. 1.

FIG. 3 is a perspective elevational cross section through the spinal cage of FIG. 2.

FIG. 4 is an elevational cross section through the cage of FIG. 2, taken along an axis perpendicular to the cross-section of FIG. 3.

FIG. 5 is a side elevational view of the cage of FIG. 1.

DETAILED DESCRIPTION OF THE PREFERRED EMBODIMENT

The present invention addresses the problem by providing implants such as intermedullary nails or spinal fusion cages that have a functional modulus of elasticity that is substantially the same as the modulus of elasticity of the native bone at the implant site. For example, implants can be provided having a functional modulus of elasticity of between about 5 GPa and about 75 GPa, typically between about 10 GPa and about 50 GPa and in some implementations between about 10 and about 30 GPa. Functional modulus means the effective modulus of the final implant, which will be the result of both the modulus of the material of the implant as well as the result of the arcuate strut architecture of the implant, as will be described below.

In addition, human or animal tissue is generally not structurally isotropic. For example, cancellous bone includes trabeculae, also referred to as spicules, defining a plurality of open spaces. The trabeculae and open spaces are generally oriented in a direction of principle stress (e.g., axially along a long bone such as a femur). The trabeculae form a porous or spongy-type tissue that is generally stiffer in a particular direction. For example, cancellous bone in the femur is generally stiffer axially than radially to accommodate an axial direction of the primary stress on the bone.

A prosthetic orthopedic implant such as a fusion cage should therefore be designed to avoid producing load concentrations which can lead to stress shielding of nearby bone. Bone can remodel to adapt to the load applied to it. If a particular location within a bone experiences increased load, the body will increase bone growth at that location.

The reverse is also true. In response to a reduced load at a particular location, the body will tend to resorb bone from that location. Therefore, concentrating stresses within a prosthetic implant providing structural support can lead to weakening and resorption of the surrounding bone.

An isotropic implant together with the anisotropy of nearby bone, can lead to stress shielding, such as if the isotropic implant is stiffer in one direction (e.g., in a radial direction, for a long bone such as a femur) than the nearby native bone. An anisotropic porous scaffold support structure can help reduce or avoid such stress shielding, such as by providing anisotropy in a similar direction to the anisotropy of the nearby native bone.

For example, the osteogenesis scaffold can be configured so that an anisotropy of a physical property, such as stiffness, compressive strength, elastic modulus, and the like, is the same or substantially the same as an anisotropy of the same physical property in the native bone in the vicinity of the intended implantation. In an example, the porous scaffold can be configured to be stiffer in a first direction (e.g., axially) compared to a second direction (e.g., laterally), such as to mimic anisotropic stiffness of nearby native bone in the first direction and second direction. The porous scaffold can be configured so that the physical property, such as stiffness, is the same or substantially the same as the same physical property in the nearby native bone in both the first direction and the second direction. In an example, "substantially the same," when referring to the matching of a physical property between the porous scaffold and the nearby native bone can refer to the value of the physical property of the porous scaffold in the first direction being within about 10% or preferably within about 5% of the value of the physical property of the nearby native bone in the first direction, such as within 3%, 1%, or less. Similarly, the physical property in the second direction can be considered to be substantially the same if the value of the physical property of the porous scaffold in the second direction is within about 10% or preferably within about 5%, or within 3%, 1%, or less of the value of the physical property of the nearby native bone in the second direction.

Referring to FIG. 1, there is illustrated a perspective view of an osteogenesis scaffold 10. The scaffold 10 can take any of a variety of configurations depending upon the intended anatomical environment, and is illustrated in FIG. 1 in the form of a spinal fusion cage 12.

Fusion cage 12 comprises a superior support surface 14, and an inferior support surface 16 spaced apart by a body portion 18. Measured in an axial direction, the anterior side 20 typically has a greater height then a posterior side 22.

The osteogenesis cage 12 comprises a plurality of arcuate struts, configured to produce an implant having a functional modulus which is a composite of the modulus of the material of construction, taken together with the physical properties attributable to the architecture of the implant. In the illustrated embodiment, the cage 12 comprises a plurality of arcuate struts configure to permit a degree of compression and expansion in the axial (superior inferior) direction, in response to cyclic physiologic load. Each arcuate strut is configured to function as a leaf spring, within the constraints imposed by the material and geometry of the struts.

In the illustrated embodiment, the superior support surface 14 comprises a plurality of struts as will be discussed. Alternatively, the superior support surface 14 and or inferior support service 16 may comprise a unitary apertured or porous plate or other construct for engaging the adjacent bony end plate.

In the illustrated embodiment, the superior support surface 14 comprises a plurality of interior surface struts 24 extending radially outwardly from a centerpoint 26 along the superior support surface 14. At least about two or four or six or eight or more interior surface struts 24 may be provided. In the illustrated embodiment, four long struts intersect at the centerpoint 26 to provide eight interior surface struts 24.

The surface struts 24 described above may be reproduced on the inferior support surface 16 in a symmetrical arrangement. The surface struts 24 may reside in a plane. Preferably, however, the surface struts 24 define an arcuate surface which is slightly convex in a direction away from the body 18, to complement the surface of the bony end plate of the adjacent vertebral body.

The superior support service 14 is spaced apart from the inferior support surface 16 by, among other things, a plurality of peripheral axial struts 28. In the illustrated embodiment, each of the radially outwardly facing ends of the surface struts 24 is connected to an axial strut 28. Thus, in the illustrated embodiment, eight axial struts 28 are positioned about the periphery of the body 18. However, any of a variety of numbers such as at least about four, six, eight, 10, 12 or more axial struts 28 maybe provided depending upon the overall desired scaffold design. Axial struts 28 maybe linear, or, preferably, each axial strut 28 may define an arc. In the illustrated embodiment, each of the axial struts 28 is concave in the direction of the central axis of the body 18. This may allow a slight axial compression of the body 18 under anatomical loads.

The intersections of the axial struts 28 and surface struts 24 are connected by a superior peripheral frame 30. In the illustrated embodiment, the peripheral frame 30 comprises a continuous annular strut, defining the outer periphery of the superior support surface 14. The inferior support surface 16 is provided with a symmetrical peripheral frame 32, defining the outer periphery of the inferior support surface 16.

Referring to FIG. 2, there is illustrated a top plan view of the superior support surface 14. A plurality of diagonal surface struts 34 join radial ends of alternating radial surface struts 24. Diagonal surface struts 34 may be nonlinear, and, in the illustrated embodiment, are arcuate with a concavity pointing in the direction of the periphery of the body 18. At least two or four or more diagonal surface struts 34 may be provided in each plane such as the superior support surface 14. In the illustrated embodiment, four diagonal service struts 34 are provided, intersecting the peripheral frame 30 at approximately 90° spacing.

The strut geometry residing in the plane of the superior support surface 14 may be symmetrically reproduced for the inferior support surface 16. That strut geometry may be further reproduced within one or two or more intermediate planes, residing in between the superior support surface 14 and inferior support surface 16.

Referring to FIG. 3, there is illustrated a vertical cross-section through a central surface strut 24. Within the body 18, a plurality of struts are provided. At least about 50%, preferably least about 80%, and typically at least about 90 or 95% of the struts are curved.

The first concave upward strut 40 extends from the peripheral frame 30 on the superior support surface 14, to the inferior support surface 16, and back to a second end of the peripheral frame 30 on superior support surface 14. A second concave upward strut 42 extends from the inferior frame 32 to the centerpoint 26 on the superior support surface 14. Each of the first second and third concave upward struts have an arcuate configuration with an upward facing concavity.

Referring to FIGS. 4 and 5, the peripheral surface of the body 18 is provided with a dock 60, for releasable engagement with an insertion tool. The dock 60 may be provided with an aperture, projection, or other surface structure (not illustrated) which is complementary to a distal portion of an insertion tool. For example, the dock 60 may be provided with a threaded aperture for threadable engagement with a threaded distal end of an insertion tool. The dock 60 is preferably provided on a peripheral surface of the implant, and maybe on the posterior, anterior, lateral or posterior lateral sides, depending upon the desired route of implantation.

In general, the implant 10 is formed as a cage having a unitary body, with openings provided through the top and bottom surfaces to form cavities or passageways throughout, wherein openings from the top surface are in communication with openings from the bottom surface and are configured and dimensioned to receive graft material, such as bone particles or chips, demineralized bone matrix (DBM), paste, bone morphogenetic protein (BMP) substrates or any other bond graft expanders, or other substances designed to encourage bone ingrowth into the cavities to facilitate the fusion. Additionally the implant 10 may be provided with side openings as shown that are also in communication with the interior cavities.

The implant 10 may be made from any of a variety of materials well known in the orthopedic implant arts. For example, implants may be made from PEEK (polyetheretherketone) such as by being machined therefrom, but alternatively, may be manufactured by injection molding or three-dimensional lithographic printing, for example. When manufactured by three-dimensional lithographic printing, implant 10 may be made of polymers, such as PEEK or other polymer and/or absorbable materials such as tri-calcium phosphate (TCP), hydroxyapatite (HA) or the like. When made of metal, implant 10 may be machined or made by metal powder deposition, for example. Alternatively, implant 10 may be made of PEKK (poly(oxy-p-phenyleneisophthaloyl-phenylene/oxy-p-phenylenetere-phthaloyl-p-phenylene) or carbon-filled PEEK. Manufacturing the implant from any of these materials make it radiolucent, so that radiographic visualization can be used to view through the implant 10 to track the post-procedural results and progress of the fusion over time. Alternatively, implant 10 could be made of titanium or other biocompatible, radiopaque metal. However, this is less preferred as this type of implant would obscure post-procedural radiographic monitoring.

Preferably, the implant comprises a metal such as titanium or a titanium alloy, manufactured using a 3D printing technology. Such technologies are known in several variations, sometimes referred to as Additive manufacturing, rapid prototyping, solid free form technology, powder bed fusion, in which a bed of powdered metal is selectively fused (through sintering or melting) by a laser or electric arc. Also, electron beam melting of metal powder (EBM) may be used.

The three-dimensional lattice configuration of the present invention, including configurations constructed from a plurality of arcuate struts may be adapted for use in a variety of orthopedic applications outside of the spine. For example, intramedullary nails for use in long bones such as the femur, tibia, fibula, radius or ulna may be constructed using the arcuate struts of the present invention, to provide an anisotropic characteristic such as modulus, to match that of the native surrounding environment. Extra medullary implants, such as plates, screws, spacers, rods, sacroiliac joint fusion implants or others may also be constructed utilizing the 3D printed arcuate strut or lattice configurations disclosed here in.

The implants disclosed herein may be provided with a porous or textured surface, such as to facilitate osteogenesis or in the case of porous surfaces, to elute drugs such as antibiotics, anticoagulants, bone growth factors or others known in the art.

Implants produce in accordance with the present invention may alternatively comprise hybrid constructs, with a first component made from 3-D printed lattice and a second component molded, machined or otherwise formed from a conventional implant material such as titanium, various metal alloys, PEEK, PEBAX or others well known in the art.

What is claimed is:

1. An osteogenesis scaffold configured for spinal fusion, comprising:
   a superior support surface;
   an inferior support surface;
   a plurality of arcuate struts separating the superior and inferior support surfaces, the plurality of arcuate struts configured to permit a predetermined amount of compression of the scaffold in a superior to inferior direction by deformation of at least some of the arcuate struts and the plurality of arcuate struts comprising a material having a strut material modulus;
   the scaffold having a functional modulus which is different than the strut material modulus and is the result of the strut modulus and the architecture of the implant.

2. The osteogenesis scaffold of claim 1, wherein each of the arcuate struts is configured to function as a leaf spring.

3. The osteogenesis scaffold of claim 1, wherein, when implanted, the plurality of arcuate struts are configured to be compressed in the superior to inferior direction and to expand to a degree, in response to a cyclic physiological load.

4. The osteogenesis scaffold of claim 1, wherein at least 80% of struts between the superior and inferior support surfaces are arcuate.

5. The osteogenesis scaffold of claim 1, wherein at least 95% of struts between the superior and inferior support surfaces are arcuate.

6. The osteogenesis scaffold of claim 1, wherein the functional modulus is within the range of from about 10 GPa to about 50 GPa.

7. The osteogenesis scaffold of claim 1, wherein the plurality of arcuate struts comprise one or more arcuate struts having a concavity facing the superior support surface.

8. The osteogenesis scaffold of claim 1, wherein the superior support surface comprises a plurality of struts.

9. The osteogenesis scaffold of claim 8, wherein the plurality of struts of the superior support surface are connected by a peripheral frame.

10. The osteogenesis scaffold of claim 1, wherein the inferior support surface comprises a plurality of struts.

11. The osteogenesis scaffold of claim 10, wherein the plurality of struts of the inferior support surface are connected by a peripheral frame.

12. The osteogenesis scaffold of claim 1, wherein the superior support surface and the inferior support surface comprise symmetrical strut geometries.

13. The osteogenesis scaffold of claim 1, wherein the superior support surface and the inferior support surface each comprise openings in communication with one another and sized to receive a graft material.

14. The osteogenesis scaffold of claim 1, comprising one or more intermediate support surfaces between the superior support surface and the inferior support surface.

15. The osteogenesis scaffold of claim 1, comprising an anterior side and a posterior side perpendicular to the superior to inferior direction, the anterior side being taller than the posterior side.

16. The osteogenesis scaffold of claim 1, comprising a dock for receiving an insertion tool.

17. The osteogenesis scaffold of claim 15, wherein the dock is located on a peripheral surface that surrounds circumferentially the plurality of arcuate struts.

18. The osteogenesis scaffold of claim 1, wherein the deformation comprises a change in a distance between opposing ends of at least some of the arcuate struts.

* * * * *